United States Patent
Zhu

(10) Patent No.: US 9,056,166 B2
(45) Date of Patent: Jun. 16, 2015

(54) INFUSION PUMP AND METHOD TO ENHANCE LONG TERM MEDICATION DELIVERY ACCURACY

(71) Applicants: Baxter International Inc., Deerfield, IL (US); Baxter Healthcare S.A., Glattpark (Opfikon) (CH)

(72) Inventor: Hong Zhu, Buffalo Grove, IL (US)

(73) Assignees: BAXTER INTERNATIONAL INC., Deerfield, IL (US); BAXTER HEALTHCARE SA, Glattpark (Opfikon) (CH)

(*) Notice: Subject to any disclaimer, the term of this patent is extended or adjusted under 35 U.S.C. 154(b) by 224 days.

(21) Appl. No.: 13/746,061

(22) Filed: Jan. 21, 2013

(65) Prior Publication Data

US 2014/0207057 A1 Jul. 24, 2014

(51) Int. Cl.
*A61M 5/172* (2006.01)
*A61M 5/142* (2006.01)
*A61M 5/168* (2006.01)
*A61M 5/145* (2006.01)

(52) U.S. Cl.
CPC ......... *A61M 5/1723* (2013.01); *A61M 5/14228* (2013.01); *A61M 5/14212* (2013.01); *A61M 5/1454* (2013.01); *A61M 5/16831* (2013.01); *A61M 2005/14208* (2013.01); *A61M 2005/14506* (2013.01); *A61M 2205/3334* (2013.01); *A61M 2205/3341* (2013.01); *A61M 2205/3355* (2013.01); *A61M 2205/702* (2013.01)

(58) Field of Classification Search
CPC ............... A61M 5/142; A61M 5/172; A61M 2001/1039; A61M 2001/1041; A61M 2001/1049; A61M 1/1081; A61M 2001/1082; A61M 2005/14208

USPC .............................................. 604/65, 67, 131
See application file for complete search history.

(56) References Cited

U.S. PATENT DOCUMENTS

| | | | | |
|---|---|---|---|---|
| 4,137,011 A * | 1/1979 | Rock | ................................ | 417/22 |
| 4,137,913 A * | 2/1979 | Georgi | ............................ | 604/67 |
| 4,534,756 A * | 8/1985 | Nelson | ........................... | 604/505 |
| 4,557,726 A * | 12/1985 | Reinicke | ......................... | 604/67 |
| 4,832,689 A * | 5/1989 | Mauerer et al. | .................. | 604/67 |
| 5,018,945 A | 5/1991 | D'Silva | | |
| 5,205,819 A * | 4/1993 | Ross et al. | ....................... | 604/67 |
| 5,399,166 A | 3/1995 | Laing | | |
| 6,966,895 B2 * | 11/2005 | Tribe | ............................ | 604/155 |

FOREIGN PATENT DOCUMENTS

WO WO 98/31935 7/1998
WO WO 02/070047 A1 9/2002

OTHER PUBLICATIONS

Int'l. Search Report issued in Int'l. App. No. PCT/US2014/011306, mailed Apr. 28, 2014.

* cited by examiner

*Primary Examiner* — Quynh-Nhu H Vu
(74) *Attorney, Agent, or Firm* — Greer, Burns & Crain, Ltd.

(57) ABSTRACT

An infusion pump is provided for pumping fluid though an administration set at a constant flow rate. The pump includes a pumping mechanism for pumping fluid and operates at a pulse frequency, and a controller controls the pulse frequency. Additionally, the pump has one or more sensors configured for measuring at least one characteristic value relating to a status of the infusion pump. The controller is configured for causing the pumping mechanism to operate at a first pulse frequency, and the one or more sensors measure the characteristic value intermittently. When the measured characteristic value meets a threshold value, the controller causes the pumping mechanism to operate at a second pulse frequency different from the first pulse frequency.

17 Claims, 5 Drawing Sheets

INFUSION PUMP AND METHOD TO ENHANCE LONG TERM MEDICATION DELIVERY ACCURACY

FIELD OF THE INVENTION

The present invention relates to a method of medication delivery, and more particularly to a method for accurately delivering medication via an infusion pump over a long duration.

BACKGROUND

Various medications may be provided to a patient via infusion, facilitated by an infusion pump such as a peristaltic pump. Peristaltic pumps typically operate by directly manipulating an administration set through which the medication is delivered. Over time, the manipulation causes a physical degradation of the administration set in the area manipulated by the infusion pump. That is, prolonged physical manipulation of the administration set by the peristaltic pump causes a reduction in springback or flexibility of the administration set tube, thereby reducing the fluid volume in each pumping cycle. As shown in FIG. 1, use of conventional pumping techniques causes an unacceptable change in the percent error of fluid volume pumped as the pumping duration increases.

Additionally, guidelines issued by the Centers for Disease Control suggest that an infusion pump should use the same administration set for no more than one week. Accordingly, infusion pump manufacturers provide pumps capable of accurately delivering the infusion fluid over a long duration (for example 72-96 hours). However, as discussed above, fatigue of the administration set results in significant error over time.

One solution to this decreased accuracy is to change administration sets more frequently. These frequent administration set changes, however, increase hospital costs by both increasing both physical resources consumed (i.e., more administration sets are used for each patient) and time required for patient care (i.e., a caregiver is required to spend more time with each patient due to more frequent administration set changes).

Another solution is to incorporate a feedback mechanism, such as a flow sensor, into the infusion pump. However, such a flow sensor would likely increase costs and be potentially difficult to integrate into the infusion pump. Moreover, conventional flow sensors generally lack the dynamic range and accuracy required to monitor infusion flow.

Accordingly, there is a need for increasing accuracy of medication delivery using infusion pumps and administration sets over a long duration without unduly increasing costs associated with medication delivery.

SUMMARY

An infusion pump including a feedforward control mechanism to control a pulse rate of the pump addresses these needs. The feedforward design allows for relatively simple control of the pulse rate of the pump, without need to integrate an expensive flow sensor. Additionally, the feedforward control allows for use of a single administration set for a relatively long duration.

In a first aspect, an infusion pump is provided for pumping fluid though an administration set at a constant flow rate over a long duration (e.g., 72-96 hours). The pump includes a pumping mechanism for pumping fluid operating at a pulse frequency, and a controller for controlling the pulse frequency. Additionally, the pump has one or more sensors configured for measuring at least one characteristic value relating to a status of the infusion pump. The controller causes the pumping mechanism to operate at a first pulse frequency, and the one or more sensors measure the characteristic value intermittently. When the measured characteristic value meets a threshold value, the controller causes the pumping mechanism to operate at a second pulse frequency different from the first pulse frequency.

In a second aspect, an infusion pump for pumping fluid though an administration set at a constant flow rate over a long duration is provided. The pump includes a pumping mechanism for pumping fluid by compressing the administration set, and operates at a pulse frequency. One or more pressure sensors connected to the pumping mechanism are configured for measuring a springback force of the administration set after being compressed by the pumping mechanism. A controller controls the pulse frequency of the pumping mechanism, and causes the pumping mechanism to operate at a first pulse frequency. The one or more pressure sensors measure the springback force intermittently, and when the springback force is lower than a threshold value, the controller causes the pumping mechanism to operate at a second pulse frequency different from the first pulse frequency.

In a third aspect, an infusion pump is provided for pumping fluid through an administration set at a constant flow rate over a long duration. The pump includes a pumping mechanism for pumping fluid operating at a pulse frequency. A controller controls the pulse frequency and causes the pumping mechanism to operate at a first pulse frequency for a period of time. After the period of time has elapsed, the controller causes the pumping mechanism to operate at a second pulse frequency greater than the first pulse frequency.

DETAILED DESCRIPTION

Figure 1:
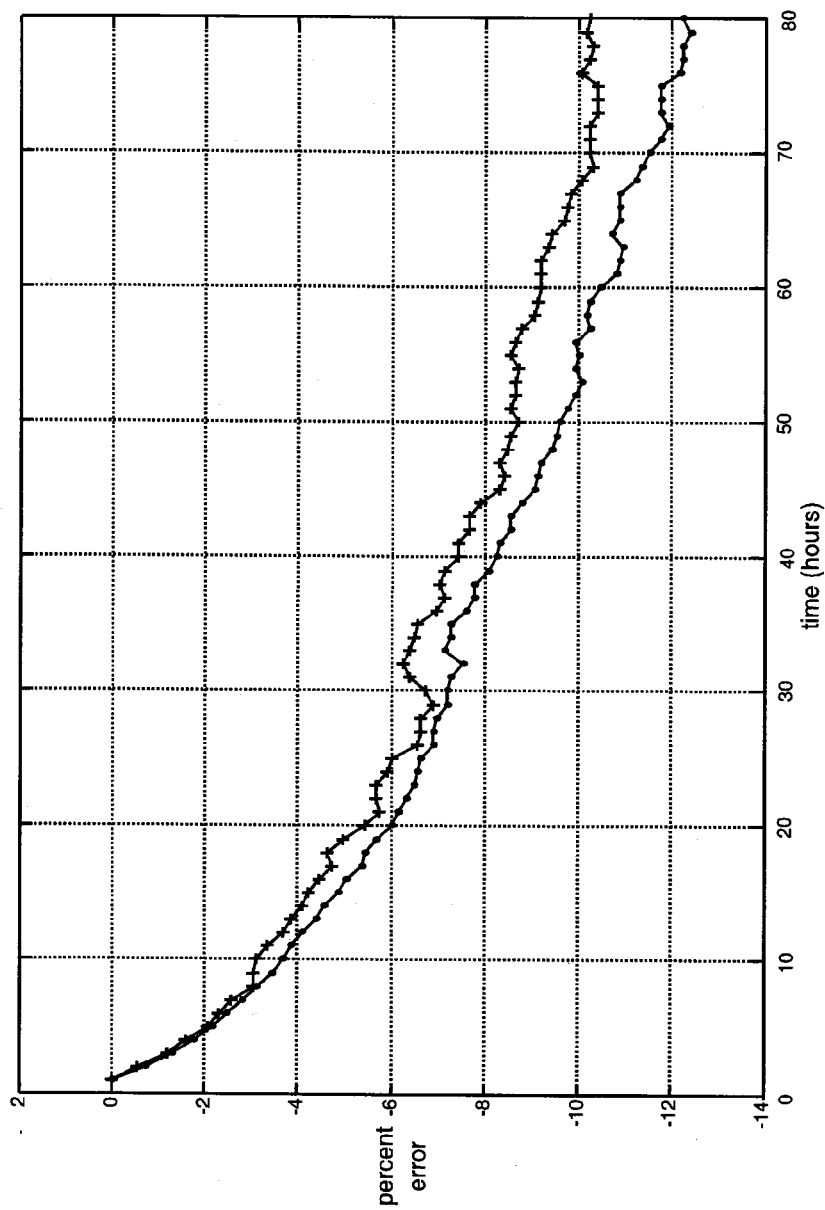
FIG. 1 shows accuracy degradation over time for conventional infusion pumps using an open loop control system.
Figure 2:
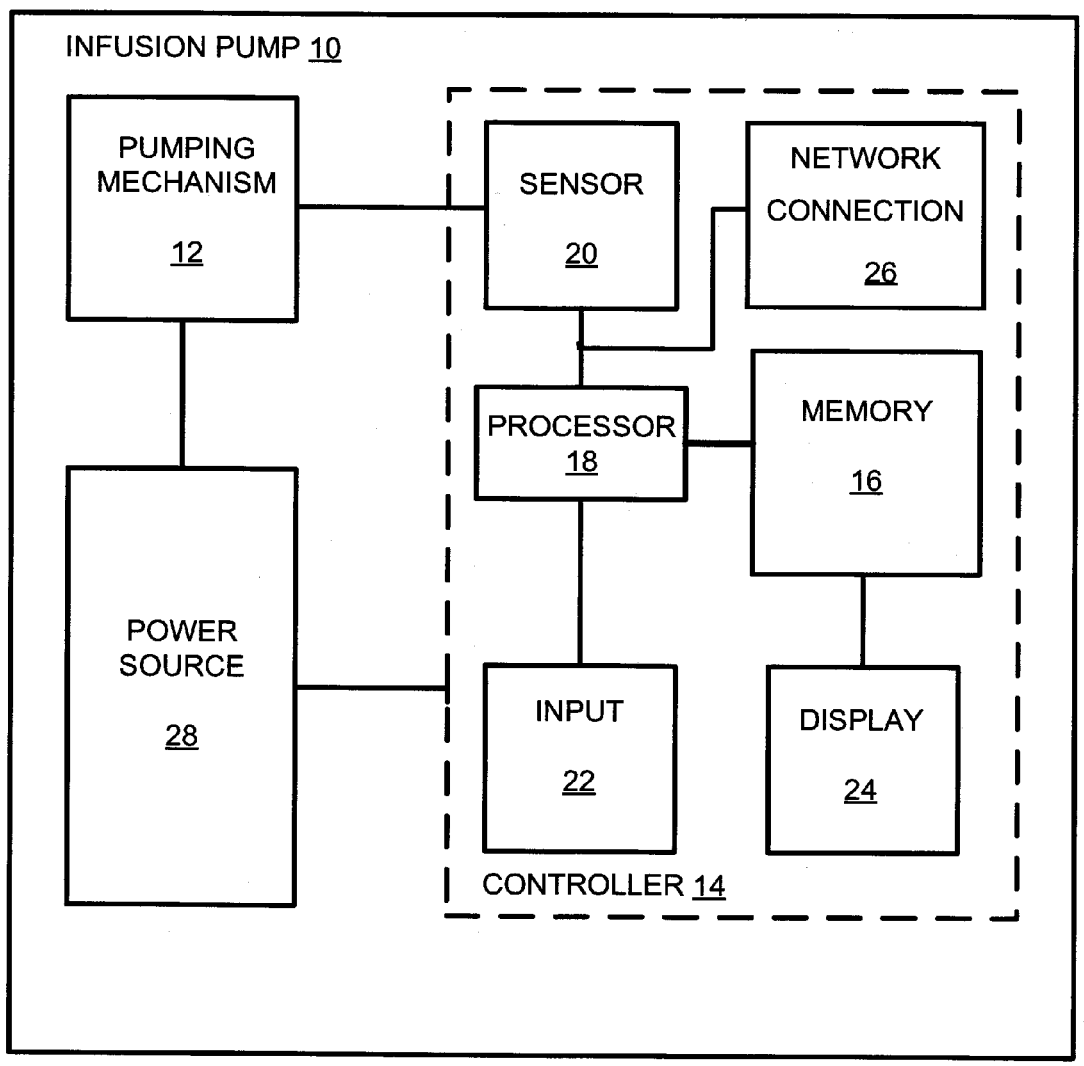
FIG. 2 is a schematic diagram of the present infusion pump.

Referring now to FIG. 2, an infusion pump 10, such as a linear peristaltic infusion pump, is shown schematically. The infusion pump 10 includes at least a pumping device 12 and a controller 14, such as a computerized device having at least a memory 16, a processor 18, one or more sensors 20, an input device 22, a display 24, and preferably a network or other communication interface 26. A power source 28 is preferably also incorporated into the infusion pump 10.

The pumping device 12 may be any pump mechanism useful to facilitate fluid flow in a large-volume infusion pump. As a non-limiting example, a linear peristaltic pump is considered suitable and discussed herein. Other non-limiting examples include multi-finger peristaltic pumping mechanisms; single finger peristaltic pumping mechanisms and rotary pumps that act along a tube length to propel fluid through a tube.

The controller 14 is preferably incorporated into the infusion pump 10, and is used to control the pumping device 12. It is preferable that the memory 16 is a non-transitory computer-readable recording medium, such as a read only memory (ROM), random access memory (RAM), hard disk, non-volatile flash memory or other electronically erasable programmable read-only memories (EEPROMs), or optical or magneto-optical memory storage media. Preferably, the memory 16 stores at least instructions which, when executed, facilitate control of the pumping device 12. The processor 18 is preferably a microprocessor or other central processing unit capable of executing the instructions stored in the memory 16.

The controller 14 also includes one or more sensors used to monitor at least one characteristic value relating to a status of the infusion pump 10. Non-limiting examples of this characteristic value include an amount of time that has elapsed during the infusion process, and a springback force of the administration set loaded in the infusion pump. Those of skill in the art will recognize that other characteristic values may be monitored without departing from the scope of this invention. Because each of the sensors 20 monitors a characteristic value related to the pumping process of the infusion pump, the sensors are connected to the pumping device 12.

A keypad or similar device that accepts data input by a user serves as the input device 22. The display 24 is a liquid crystal display, cathode ray tube, plasma display, or other device capable of outputting data from the memory and processor in a way that is easily discernible by a user. Alternatively, the input device 22 and display 24 may be incorporated into a single input/output device such as a touch screen display. The input device 22 and/or display 24 may be integral with the infusion pump 10, or may be separate from the infusion pump 10 provided the input device 22 and/or display 24 are adapted for bi-directional communication with the infusion pump 10.

The network communication interface 26 allows the infusion pump 10 to connect to a local area network (LAN), wide area network (WAN), and/or the Internet. The network connection may be a wired connection using, for example, the IEEE 802.3 standard, or a wireless connection using standards such as IEEE 802.11 a/b/g/n/ac, or any newly developed standards that supersede these. Additionally, the network connection 26 may connect to a cellular/mobile data network using a protocol such as LTE, WiMAX, UMTS, CDMA, HSPA, HSPA+, GPRS, and the like.

The power source 28 is any known power source sufficient to provide power to both the pumping device 12 and the controller 14. As non-limiting examples, the power source 28 may include one or more of a battery, a fuel cell, and a connection to a power line.

In operation, conventional peristaltic pumps are used to convey fluid from an upstream source container, through an intravenous (IV) tube of an administration set in a downstream direction towards and into a patient through an access site. Conventional peristaltic pumps rely on one or more occluders sequentially compressing a pumping section of a flexible tube. The pumping section being that portion of the tube adjacent with the occluders. With a primed tube (one already filled with fluid) the upstream occluder compresses the tube, followed in sequence by the next downstream occluder, until each of the occluders present has compressed the tube. As the occluders apply pressure to the tube, the part of tube under compression is pinched closed (occluded), thus forcing the fluid to move downstream through the tube. When compression by all of the occluders is complete or nearly complete, the upstream occluder begins to re-open, or decompress, the tube. The opening of the occluders also occurs sequentially from the upstream direction towards the downstream direction. As the tube decompresses or re-opens to its natural state after release of the occluder, fluid flows into the pumping section of the tube from the source container under the force of gravity and ambient pressure. The extent to which the pumping section of the tube re-opens depends upon the current elasticity of the pumping section of the tube. Therefore, the amount of fluid that flows into the pumping section as or after the occluders have opened is also dependent upon the elasticity of the pumping section of the tube.

However, the mechanical manipulation of the flexible tube by the occluders leads to a physical breakdown of the tube, whereby the flexible tube no longer fully re-opens to its original shape. Accordingly, over time, the fluid volume moved through each cycle of the pump is reduced, leading to an overall reduction in the infusion fluid provide to a patient. Moreover, traditional infusion pumps rely on an open-loop control to maintain a flow rate by maintaining pulse rate, and do not take this reduction in provided volume into account. Accordingly, pump accuracy degrades over time. It should be noted that in the above described sequence of compression by the occluders, at all times, at least one occluder remains compressed at any given time to prevent a free-flow condition as is known in the art. Also, the pumping may be accomplished with a single occluding member. This case would include that addition of an upstream valve located upstream of the occluding member and a downstream valve located downstream of the occluding member. Compression and release of the upstream valve, occluding member and downstream valve are sequenced as is known in the art to achieve the desired fluid movement.

After an administration set is properly loaded into the infusion pump 10, the material used to form the administration set is specified. This may require a manual specification by the user, such as through an entry of the specific material (e.g., DEHP, non-DEHP, polyethylene, etc.) and/or a model number corresponding to the loaded set using the input device. Alternatively, some embodiments may include, as in input device, a reader capable of reading a barcode, QR code, or other similar machine-readable code to input the model of the administration set. Still other embodiments of the infusion pump are suitable for use with only administration sets formed from a particular material, or with only a particular model of administration set. In this case, the material is specified automatically, or presumed, without requiring user interaction.

Infusion parameters such as flow rate, volume, and/or duration are set by the user, or as is otherwise known. The flow rate and the specified type of administration set are used to calculate a pulse rate for the pumping device. That is, the volume of fluid moved through the pump in each cycle for a particular administration set is known. For example, the volumes may be empirically determined through large-scale testing. Accordingly, the number of pulses required to establish the flow rate set by the user can be determined based on the formula:

$$\text{pulse frequency} = (\text{calibrated pulses}/\text{calibrated volume}) * V_i, \text{ where } V_i \text{ is the flow rate.}$$

The flow rate and/or the pulse frequency may be used to normalize the amount of time that an administration set may be used for before being changed (i.e., the lifespan of the administration set). As a non-limiting example, if an administration set may be used for 72 hours at a flow rate of 125 ml/hr, the time that the same type of administration set may be used at other flow rates is shown in Table 1 below:

TABLE 1

Time normalization for different flow rates

| | Flow Rate (ml/hr) | | | | | |
|---|---|---|---|---|---|---|
| | 0.1 | 1 | 10 | 125 | 400 | 999 |
| Normalization ratio | 0.01 | 0.05 | 0.3 | 1 | 2.88 | 7.2 |

As shown in Table 1, if it is recommended that an administration set be replaced after 72 hours of use at a flow rate of 125 ml/hr, the same type of administration set should be replaced after 10 hours of use at 999 ml/hr. The table is stored, for example, in the memory 16 of the controller 14. In addition to the stored values, linear interpolation may be used to calculate normalization factors for flow rates between the stored data points. The normalization ratios shown in Table 1 are illustrative only. Different ratios may be stored in place of and/or in addition to those shown in Table 1 without departing from the scope of the invention.

Once the first pulse frequency is calculated, the controller 14 controls the pumping mechanism 12 to begin pumping at the first pulse frequency, and a time mark established, indicating when the flow began.

Additionally, a feedforward delay time is determined based on the flow rate and type of administration set. The feedforward time delay represents the amount of time the infusion pump should be run using a particular administration set type before the accuracy degrades to an unacceptable level. As an example, an unacceptable level may be determined to be an error of 5%. Larger or smaller error levels may be used, depending on standards of the health care facility or other factors. Feedforward time delay periods are preferably empirically derived, but may also be calculated mathematically. An example feedforward time delay for an administration set which has a life span of 72 hours and is being used to deliver medication at a flow rate of 125 ml/hr is approximately 24 hours. That is, after each 24 hour time period has elapsed, the pulse rate of the pump should be adjusted to maintain acceptable accuracy for long-duration pumping. As with the lifespan, the feedforward time delay is adjusted based on the normalization ratio. Accordingly, if an administration set has a feedforward time delay of 24 hours at 125 ml/hr (normalization ratio=1), the same administration set would have a feedforward time delay of 3.33 hours at a flow rate of 999 ml/hr (normalization ratio=7.2). While this example provides concrete values for the feedforward time delay, the values are merely intended to be exemplary, and those of skill in the art will recognize that feedforward delays longer or shorter than example of 24 hours are within the scope of the present invention.

In addition to the feedforward delay, a compensation factor is determined. The compensation factor represents the amount of change required to the flow rate, and is governed by the particular administration set in use, the desired flow rate, and amount of time that the administration set has been in use. Compensation factors are preferably stored within memory 16 in a tabular format, in correspondence with the administration set, the flow rate, and the number of feedforward time delay periods elapsed. An example table for a particular administration set is shown below in Table 2:

TABLE 2

Compensation factor for a particular administration set

| | Flow rate (ml/hr) | | | | | |
|---|---|---|---|---|---|---|
| | 0.1 | 1 | 10 | 125 | 400 | 999 |
| First feedforward time delay | Delta1a | Delta2a | Delta3a | Delta4a | Delta5a | Delta6a |
| Second feedforward time delay | Delta1b | Delta2b | Delta3b | Delta4b | Delta5b | Delta6b |

As shown above, compensation factors (collectively, "delta") corresponding to common or otherwise useful flow rates are stored in the table. Compensation factors for other flow rates can be calculated by, for example, linear interpolation.

The pulse frequency is adjusted by the compensation factor such that a new pulse frequency is set according to the equation:

New pulse frequency=((calibrated pulses+delta)/calibrated volume)*$V_i$, where $V_i$ is the flow rate.

In an alternate embodiment, the one or more sensors 20 may include a pressure sensor connected one or more of the occluders in the pumping mechanism 12. The pressure sensor is preferably used in a linear peristaltic infusion pump.

Figure 3A:
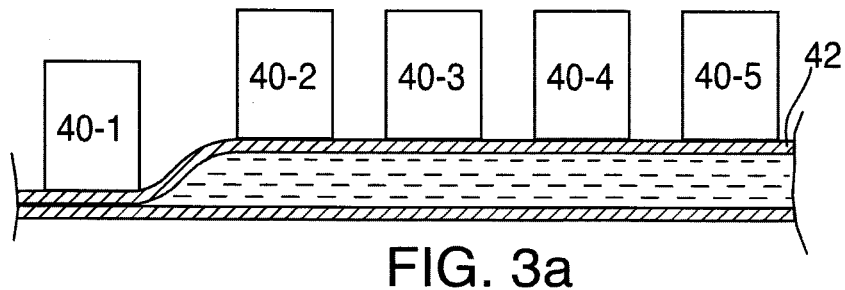
FIGS. 3a-3d illustrate a technique used by the infusion pump of FIG. 2 to measure springback force of an administration set.
Figure 3B:
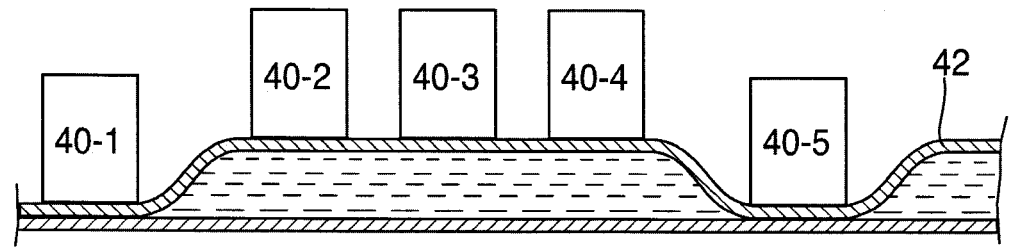
Figure 3C:
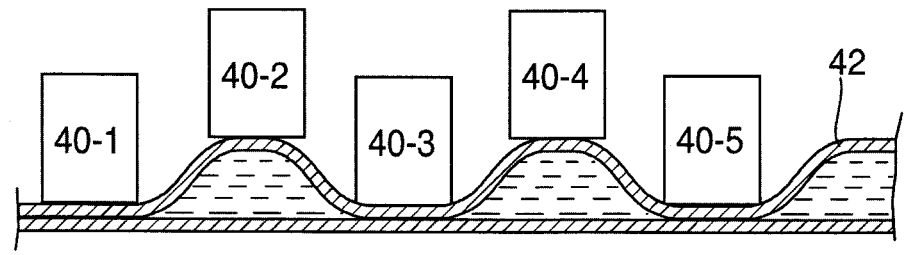
Figure 3D:
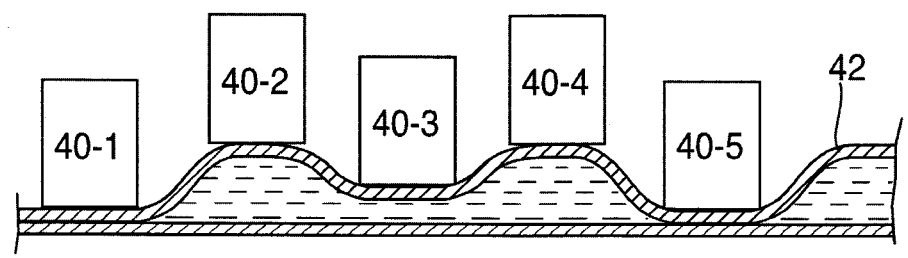

A process for measuring the springback force of the administration set using a pressure sensor in a linear peristaltic pump is illustrated in FIGS. 3a-3d. As shown in FIG. 3a, a downstream occluder 40-1, disposed at the downstream end of the pump 12, fully compresses a portion of a tube 42 of the administration set, allowing fluid to fill an upstream portion of the administration set. Next, as shown in FIG. 3b, occluder 40-5, disposed at the upstream end of the pump 12, fully compresses the tube 42. Thereafter, centrally-disposed occluder 40-3, which incorporates the pressure sensor, compresses the tube 42 to a calibrated depth as shown in FIG. 3c. Then, as shown in FIG. 3d, occluder 40-3 is released, and the incorporated pressure sensor measures the springback force of the tube 42. While the pumping mechanism 12 shown in FIGS. 3a-3d includes 5 occluders, those of skill in the art will recognize that more or fewer occluders may be used without departing from the scope of the invention.

As above, infusion parameters such as flow rate, volume, and/or duration are set by the user. The springback force measurement technique described above may be used prior to operation of the pump 12 for identifying the material from which the administration set is formed. That is, each different material preferably includes a unique initial springback force. Accordingly, the initial springback force measurement may be used to accurately identify the material used to form the administration set. Preferably, a user is asked to confirm the material of the administration set. The infusion process then begins with the controller 14 controlling the pumping mechanism 12 to operate at a pulse frequency determined using the pulse frequency equation above, based on the administration set material and the set flow rate.

Figure 4:
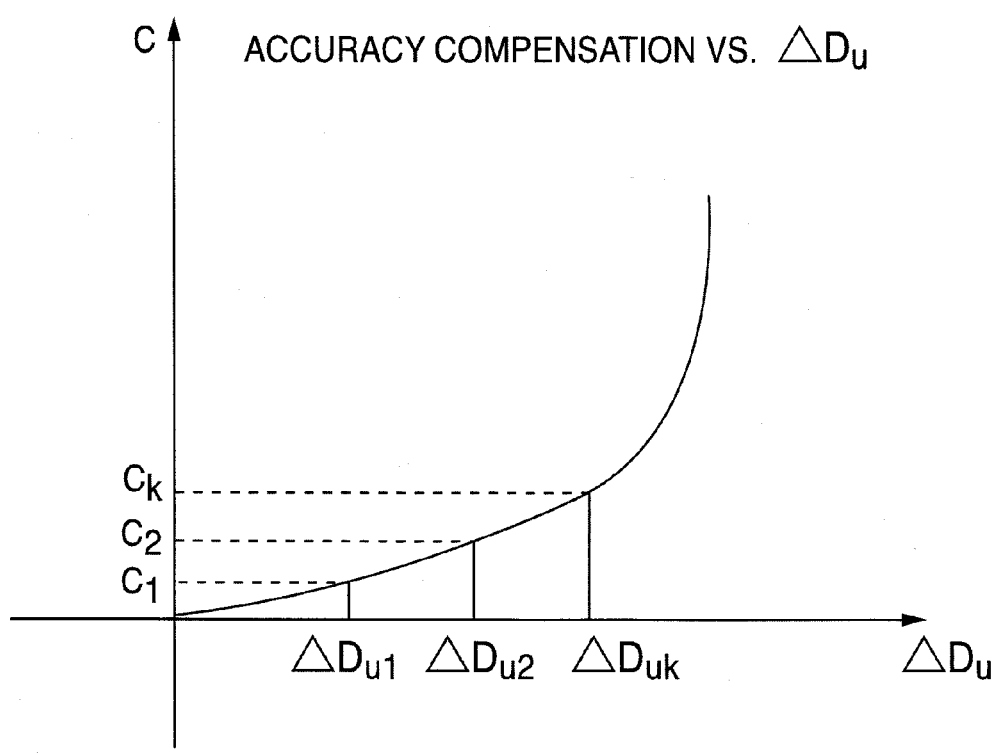
FIG. 4 shows an example curve plotting a change in springback force and a compensation factor.

Thereafter, the springback force is measure intermittently to verify that the springback force has not decayed past a threshold value. FIG. 4 shows a typical curve representing tube fatigue change $\Delta D_u$, measured by the springback force, and compensation factor C. As shown in the curve, when the tube fatigue change reaches a limit $\Delta D_{uk}$, the compensation factor C rises abruptly. Accordingly, it is preferable that the administration set be changed when the fatigue change reaches limit $\Delta D_{uk}$. Fatigue change thresholds $\Delta D_{u1}$ and $\Delta D_{u2}$ are selected based on a material used to form the administration set. When the measured springback force reaches these selected thresholds, the pulse frequency is adjusted according to the equation:

New pulse frequency=((calibrated pulses+C)/calibrated volume)*$V_i$, where $V_i$ is the flow rate.

Threshold values $\Delta D_{u1}$ and $\Delta D_{u2}$ for each administration set are preferably stored in memory, but may also be calculated. Because this technique relies on actual fatigue measurements, it is not necessary to normalize the threshold values based on flow rate. However, incorporating the pressure sensor into the pumping mechanism 12 raises manufacturing costs of the infusion pump.

For all above embodiments, there are two main sources of error which degrade the accuracy of the infusion pump 12 if not managed appropriately. First, the time mark registration is important. If the time mark is registered incorrectly, it becomes difficult to determine when time equal to a feedforward time delay has elapsed, contributing to accuracy degradation. Second, overcompensation by the feedforward control, due to, for example, variation in environment or material can degrade accuracy of the pump 12.

The time mark is established when the user confirms the type of administration set. Accordingly, preventing the user from confirming an administration set while the door is open is desirable to help ensure that the time mark is accurately established at the time the infusion begins. To that end, a sensor may be sued to determine when the door of the infusion pump 10 is open, and the controller 14 may prevent the user from confirming the type administration set while the door is open.

Another factor affecting the accuracy arises in cases necessitating tube reloading. For example, if an administration set is re-loaded during an infusion, it is important that the set be reloaded such that the pumping mechanism 12 is acting on the same portion of the set. That is, only the portion of the set being acted on by the pumping mechanism 12 degrades. Accordingly, known methods are used to ensure that the administration set is reloaded in the same position consistently.

Preferably, the one or more sensors 20 include a Hall, or other sensor, for detecting whether a door of the infusion pump is open. The sensors 20 preferably also include an air in line sensor to detect the presence of an air bubble in the fluid passing through the administration set. Air bubbles present in the liquid typically necessitate "priming" of the pump, which is typically a manual process known in the art to remove air bubbles, and which requires remove and reloading of the administration set. Typically, the pump is stopped, the door is opened and the tube or set is removed. Then the user manually advances the air bubble to a portion of the tube that includes a feature that would enable removal of the air bubble via, for instance, a syringe.

To reduce the need for such manual priming, functionality has been added to the infusion pump that allows for a temporary increase in the flow rate, causing the air bubble to advance to a position where it can be removed using, for example, a syringe.

Figure 5:
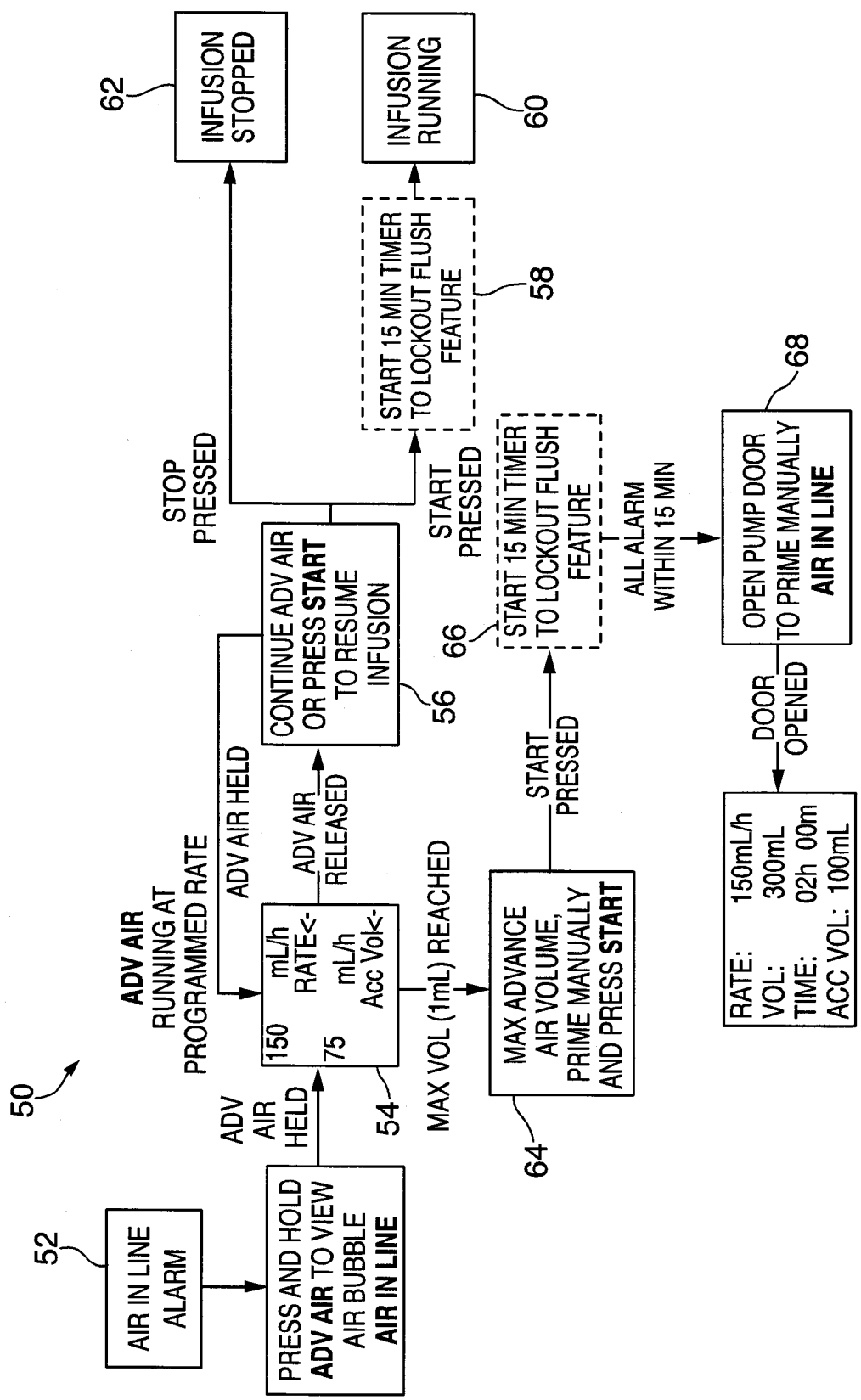
FIG. 5 is a flowchart showing a procedure for advancing air bubbles through the administration set using the infusion pump of FIG. 2.

Referring now to FIG. 5, a flowchart showing the procedure for advancing the air bubble and the user prompts presented at each step in the procedure is generally labeled 50. At step 52, an alarm indicating air in the line is triggered. In response, the user can press and hold an air advance key at step 54. While the key is held, the infusion pump is run at an increased flow rate (and a correspondingly increased pulse frequency). When the user releases the air advance key, a prompt is displayed requesting that the user continue pressing the air advance key to continue the air advance process, or press "start" to resume the infusion at step 56. If the user presses "air advance," the process returns to step 54.

If the user presses "start," a timer locking out the air advance flush feature for a predetermined time preferably begins to run in step 58, and the infusion resumes in step 60. Alternatively, if the user presses "stop," the infusion is halted in step 62. Because the increase in flow rate used to advance the air bubble also causes an increase in the rate of infusion to the patient, the amount that the air bubble can be advanced is limited. Preferably, the advance is limited to approximately 1 ml of fluid, though other limits are contemplated. In step 64, when the maximum advance volume is reached, a notice is displayed to the user that the pump should be manually primed to remove the air bubble. A timer locking out the air advance flush feature for a predetermined time preferably begins to run in step 66. The length of this timer may differ from the timer set in step 58, if desired. As shown in step 68, if the air in line alarm is triggered while the timer prevents the air advance flush feature, a notification is displayed to the user indicating that the line should be manually primed.

Sensors 20 may also include, for example a drip-drop sensor, which serves as a redundant check to help avoid gross inaccuracies in the infusion rate. Additionally, a temperature sensor is included among the sensors 20. As is known in the art, physical properties of the pump and the administration set are affected by the ambient temperature. In particular, infusion pumps are typically inaccurate in temperatures below 15° C. or above 38° C. Accordingly, if the ambient temperature is less than 15° C. or greater than 38° C., the infusion pump is disabled. Even at temperatures within the operative range (i.e., 15° C.-38° C.), it may be desirable to alter the normalization ratio to improve accuracy. For example, at temperatures less than about 18° C., the normalization ratio may be reduced to about one third of the ratio provided in Table 1.

While the principles of the present infusion pump and method for enhancing long term medication delivery accuracy have been described above in connection with specific apparatus and applications, it is to be understood that this description is made only by way of example and not as a limitation on the scope of the claims following below.

What is claimed is:

1. An infusion pump for pumping fluid though an administration set at a constant flow rate over a long duration, the pump comprising:
   a pumping mechanism configured for pumping fluid, said pumping mechanism operating at a pulse frequency; and
   a controller for controlling said pulse frequency of said pumping mechanism; and one or more sensors capable of measuring at least one characteristic value relating to a status of said pumping mechanism;
   said controller configured for operating said pumping mechanism at a first pulse frequency;
   said one or more sensors measure said at least one characteristic value intermittently; and
   wherein when said at least one characteristic value meets a threshold value, said controller causes said pumping mechanism to operate at a second pulse frequency, said second pulse frequency being different from said first pulse frequency; wherein said threshold value is calculated based on a material used to form the administration set.

2. The infusion pump of claim 1, wherein at least one of said one or more sensors is a timer, and wherein said threshold value is an elapsed time.

3. The infusion pump of claim 1, wherein the pumping mechanism is capable of pumping fluid by compressing the administration set, and
wherein at least one of said one or more sensors is a pressure sensor sensors connected to said pumping mechanism and capable of measuring a springback force of the administration set after being compressed by said pumping mechanism.

4. The infusion pump of claim 1, further comprising an air advance mechanism for temporarily increasing said pulse frequency to allow for an increased flow rate for the duration of pumping approximately 1 ml of the fluid.

5. The infusion pump of claim 1, wherein said calculated threshold value is also based on a flow rate.

6. The infusion pump of claim 1, said threshold value is a first threshold value, and wherein when said characteristic value measured by said one or more sensors meets a second threshold value different than said first threshold value, said controller causes said pumping mechanism to operate at a third pulse frequency, said third pulse frequency being greater than said first pulse frequency and said second pulse frequency.

7. The infusion pump of claim 1, wherein said controller causes said pumping mechanism to stop pumping if an ambient temperature is less than about 15° C. or if said ambient temperature is greater than about 38° C.

8. An infusion pump for pumping fluid though an administration set at a constant flow rate over a long duration, the pump comprising:
a pumping mechanism configured for pumping fluid by compressing the administration set, said pumping mechanism operating at a pulse frequency;
one or more pressure sensors connected to said pumping mechanism and capable of measuring a springback force of the administration set after being compressed by said pumping mechanism; and
a controller for controlling said pulse frequency of said pumping mechanism, wherein said controller causes said pumping mechanism to operate at a first pulse frequency;
said one or more pressure sensors measuring said springback force intermittently; and
when said springback force measured by said one or more pressure sensors is lower than a threshold value, said controller causes said pumping mechanism to operate at a second pulse frequency, said second pulse frequency being greater than said first pulse frequency; wherein said threshold value is calculated based on a material used to form the administration set.

9. The infusion pump of claim 8, wherein said threshold value is a first threshold value, and wherein when said measured springback force measured by said one or more pressure sensors is lower than a second threshold value smaller than said first threshold value, said controller causes said pumping mechanism to operate at a third pulse frequency, said third pulse frequency being greater than said first pulse frequency and said second pulse frequency.

10. The infusion pump of claim 8, wherein said one or more pressure sensors measure said springback force prior to operation of the pump, and the material used to form the administration set is determined based on said measured springback force.

11. The infusion pump of claim 8, wherein said springback force is measured while the administration set contains fluid.

12. The infusion pump of claim 8, further comprising an air advance mechanism for temporarily increasing said pulse frequency to allow for an increased flow rate for the duration of pumping approximately 1 ml of the fluid.

13. An infusion pump for pumping fluid through an administration set at a constant flow rate over a long duration, the pump comprising:
a pumping mechanism for pumping fluid, said pumping mechanism operating at a pulse frequency; and
a controller for controlling said pulse frequency of said pumping mechanism;
said controller is configured for causing said pumping mechanism to operate at a first pulse frequency for a period of time, and
after said period of time has elapsed, said controller is configured for causing said pumping mechanism to operate at a second pulse frequency, said second pulse frequency being greater than said first pulse frequency; wherein said period of time is calculated based on a material used to form the administration set.

14. The infusion pump of claim 13, wherein said calculated period of time is also based on a flow rate.

15. The infusion pump of claim 13, further comprising an air advance mechanism for temporarily increasing said pulse frequency to allow for an increased flow rate for the duration of pumping approximately 1 ml of the fluid.

16. The infusion pump of claim 13, wherein said period of time is a first period of time, and wherein after a second period of time longer than said first period of time has elapsed, said controller causes said pumping mechanism to operate at a third pulse frequency, said third pulse frequency being greater than said first pulse frequency and said second pulse frequency.

17. The infusion pump of claim 13, further comprising a tube presence detector configured to detect the presence of the administration set within the infusion pump.

* * * * *